United States Patent [19]

Hattori et al.

[11] Patent Number: 4,524,761
[45] Date of Patent: Jun. 25, 1985

[54] ENDOSCOPE APPARATUS

[75] Inventors: Shinichiro Hattori; Seiichi Hosoda; Takeshi Takamatsu, all of Tokyo, Japan

[73] Assignee: Olympus Optical Co., Ltd., Tokyo, Japan

[21] Appl. No.: 580,780

[22] Filed: Feb. 21, 1984

Related U.S. Application Data

[63] Continuation of Ser. No. 355,243, Mar. 5, 1982, abandoned.

[30] Foreign Application Priority Data

Mar. 16, 1981 [JP] Japan ................................. 56-37662

[51] Int. Cl.³ .............................................. A61B 1/06
[52] U.S. Cl. .......................................... 128/6; 354/62
[58] Field of Search ........................................ 128/4–8; 354/62, 416, 417

[56] References Cited

U.S. PATENT DOCUMENTS

| | | | |
|---|---|---|---|
| 3,638,543 | 2/1972 | Kando | 95/10 CE |
| 3,774,072 | 11/1973 | Ogawa | 315/151 |
| 4,153,356 | 5/1979 | Hama | 354/62 |
| 4,298,256 | 11/1981 | Kawamura et al. | 354/416 |
| 4,310,228 | 1/1982 | Terada | 128/6 |
| 4,325,618 | 4/1982 | Hosoda | 128/6 |
| 4,349,255 | 9/1982 | Takayama | 354/62 |
| 4,367,024 | 1/1983 | Takayama | 354/62 |
| 4,398,127 | 8/1983 | Bahn et al. | 354/416 |

Primary Examiner—Edward M. Coven
Assistant Examiner—Max F. Hindenburg

[57] ABSTRACT

The camera arranged at the eyepiece section of an endoscope has a photometric circuit for generating observation and photographing light control signals selectively to control the brightness of observation light and the amount of photographing light. The light supply unit has observation and photographing light control circuits, said observation light control circuit serving to control the amount of current supplied to the observation light source correspondingly to the observation light signal applied through the photometric circuit in the camera and said photographing light circuit serving to control the light irradiation time of the photographing light source or electronic flash tube correspondingly to the photographing light control signal.

7 Claims, 6 Drawing Figures

ENDOSCOPE APPARATUS

The application is a continuation of application Ser. No. 355,243, filed Mar. 5, 1982 now abandoned.

BACKGROUND OF THE INVENTION

The present invention relates to an endoscope apparatus and, more particularly, an endoscope apparatus having automatic observation-light control and automatic exposure functions.

An endoscope apparatus is generally designed to have observation and photographing functions and has been further provided with automatic light control and automatic exposure functions these days so as to enable observation and photographing to be carried out under optimum light and right exposure. In the case of conventional endoscope apparatus, however, a photoelectric element for receiving light reflected from an object is arranged in the endoscope while an exposure calculating circuit in the light supply unit, and a long signal line is employed to connect the photoelectric element to the exposure calculating circuit. When output signals of the photoelectric element pass through the signal line, therefore, noises are mixed with these output signals. This causes correctly-calculated value not to be obtained and the accuracy in automatic exposure to be lowered when the exposure calculating circuit calculates exposure on the basis of the output signals of the photoelectric element. Early-opened Japanese patent application No. Sho-55/121,879 discloses an endoscope apparatus in which the exposure calculating circuit is arranged in the endoscope camera so as to solve the drawback. In the case of this endoscope apparatus, however, the output signals of the photoelectric element are not transmitted to the light source unit, thus making it impossible to automatically control an observation light.

SUMMARY OF THE INVENTION

The object of the present invention is therefore to provide an endoscope apparatus capable of effecting automatic exposure and observation light control with high accuracy.

According to the present invention is provided an endoscope apparatus comprising an endoscope, an endoscope camera attached to the endoscope and having means for measuring the amount of light reflected from an object, and a light source unit having observation and photographing light sources, wherein the measuring means has a circuit for selectively supplying observation light control signal and photographing light control signal to the light source unit having light control means for controlling the light of observation or photographing light source correspondingly to the light control signal transmitted.

DETAILED DESCRIPTION OF THE PREFERRED EMBODIMENTS

Figure 1:
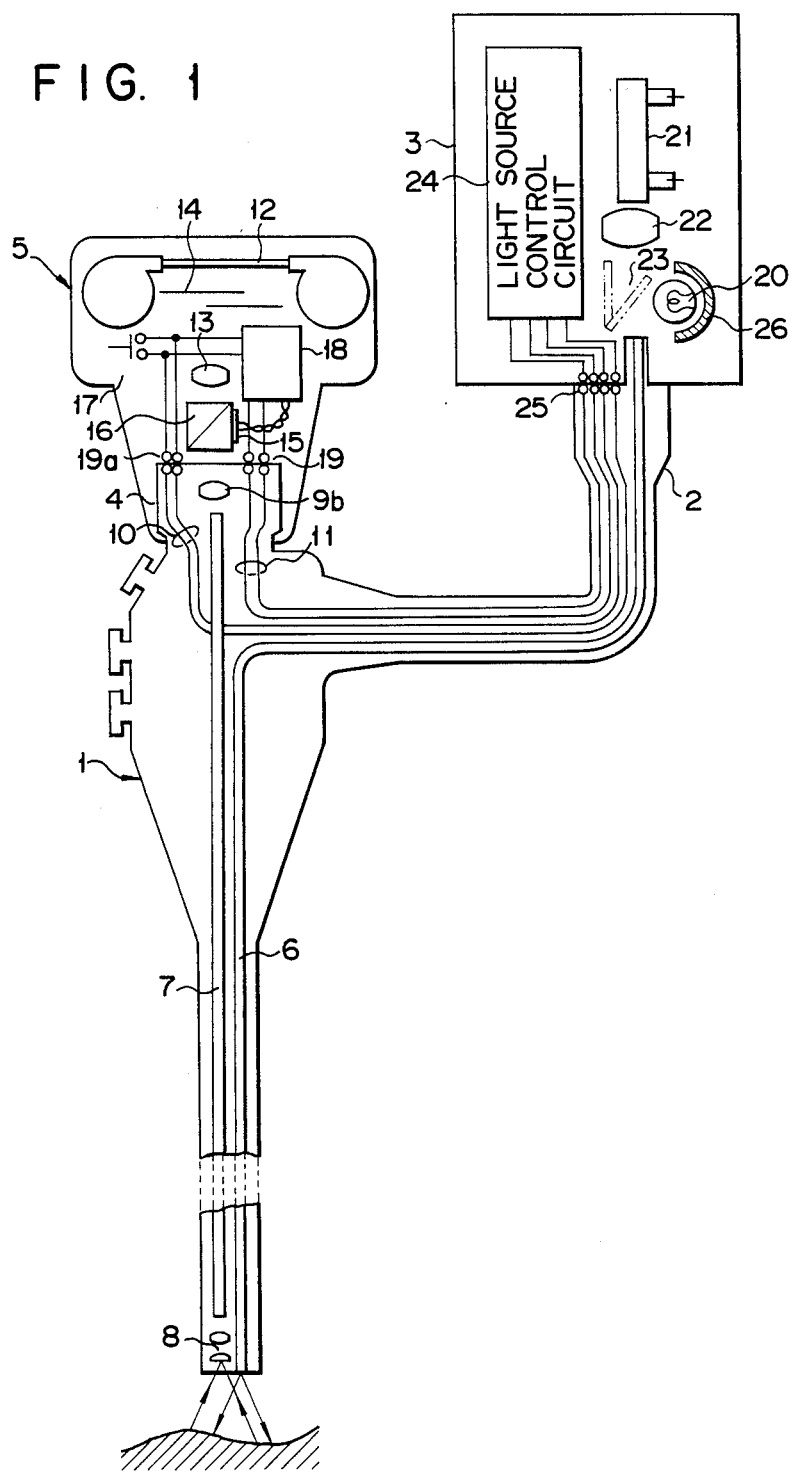
FIG. 1 schematically shows the arrangement of an endoscope apparatus according to an embodiment of the present invention.

Referring to FIG. 1, a light source connector 2 of an endoscope 1 is connected to a light source unit 3 and an endoscope camera 5 is arranged at an endoscope eyepiece section 4. Light and image guides 6 and 7 are arranged in the endoscope 1 with the one end of the image guide opposite to an objective system 8 and the other end thereof to an ocular lens 9. Release and control signal lines 10 and 11 are further arranged in the endoscope 1. A film 12 is arranged opposite to a photographing lens 13 through a shutter 14. A beam splitter 16 is arranged between the photographing lens 13 and endoscope eyepiece section 4. A photoelectric element 15 is arranged on the side of beam splitter 16 and connected to a camera control section 18. A release switch 17 is also connected to the camera control section 18. The release switch 17 is connected through a terminal 19a to the release signal line 10 and the signal output terminal of camera control section 18 is connected through a terminal 19b to the control signal line 11.

The light source unit 3 is provided with observation and photographing light sources such as halogen lamp 20 and electronic flash tube (strobo tube) 21, for example. The electronic flash tube 21 is arranged opposite to the light guide 6 with a condensing lens 22 and a light path changeover mirror 23 interposed therebetween, while the observation lamp 20 is arranged at a position perpendicular to the light path of electronic flash tube 21 and opposite to the light path changeover mirror 23. The signal input terminal of a light source unit control section 24 is connected via a terminal 25 to signal lines 10 and 11. A light focussing mirror 26 is arranged for the observation lamp 20.

Figure 2:
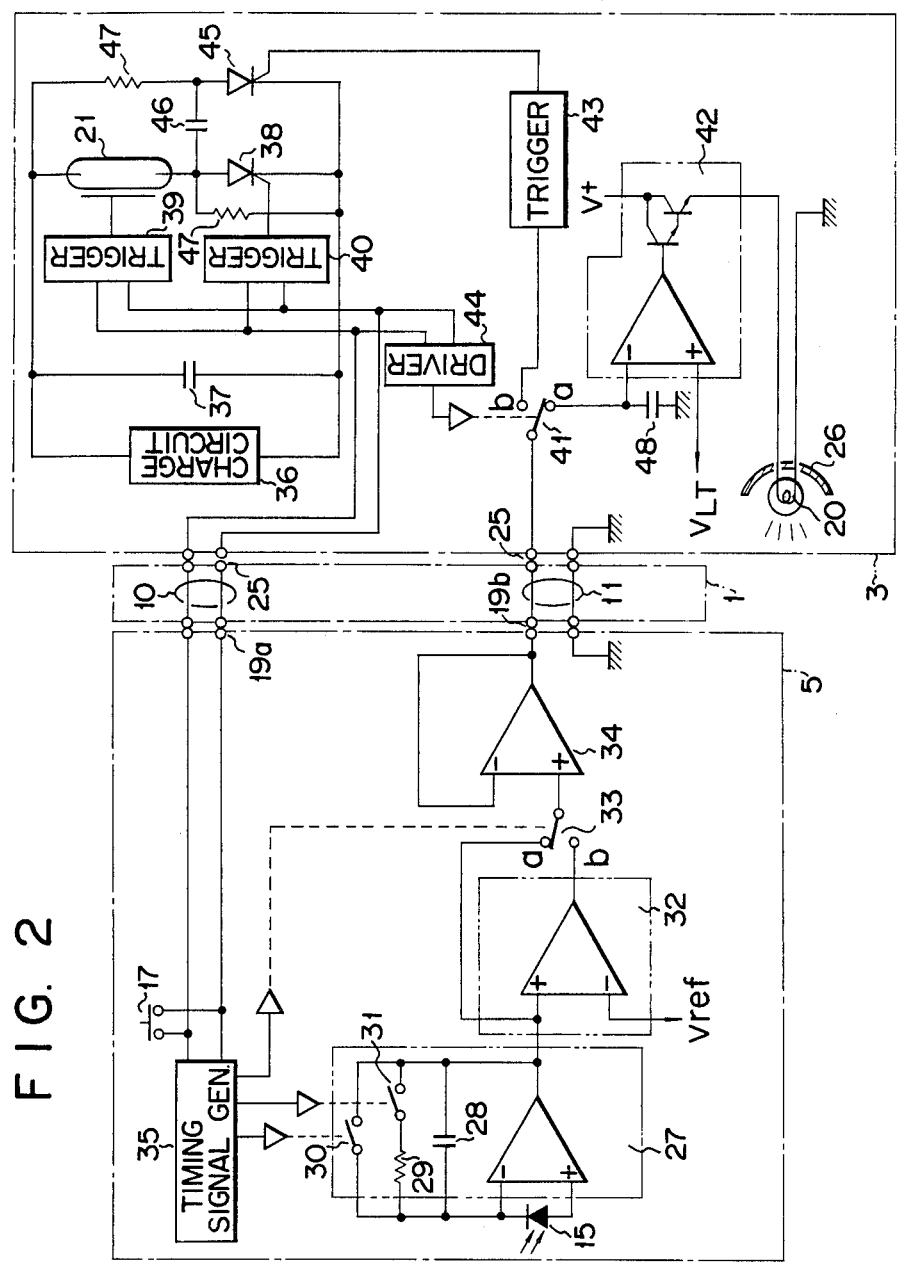
FIG. 2 is a circuit diagram of the endoscope apparatus shown in FIG. 1.

FIG. 2 shows an electric circuit of the endoscope apparatus shown in FIG. 1. According to this circuit, an integrator/current-voltage converter circuit 27 is arranged in the camera 5. A series circuit of an integrating resistor 29 and a switch 31, and a switch 30 are connected parallel to an integrating capacitor 28 in the circuit 27. The output terminal of circuit 27 is connected to a comparator 32 while to a terminal a of an analog switch 33. Another terminal b of the analog switch 33 is connected to the output terminal of the comparator 32. The output terminal of the analog switch 33 is connected to a buffer circuit 34. Associating with the operation of the release switch 17, a timing circuit 35 drives the analog switches 30, 31 and 33 at such timings as will be described later. The release switch 17 is connected through the terminal 19a, signal line 10 and terminal 25 to the trigger circuits 39 and 40 and a switch driving circuit 44. Output terminals of the trigger circuits 39 and 40 are connected to a trigger electrode in the electronic flash tube 21 and a gate electrode in the main thyristor 38, respectively. A charging circuit 36 and a main capacitor 37 are connected parallel to the series circuit of the electronic flash tube 21 and main thyristor 38. A quenching circuit constructed by a quenching capacitor 46 and a quenching thyristor 45 is connected to the main thyristor 38. The quenching capacitor 46 is charged by the current flowing through a charging resistor 47.

The output terminal of the buffer circuit 34 is connected to the input terminal of an analog switch 41 via the terminal b, signal line 11 and terminal 25. A terminal a of the analog switch 41 is connected to a observation light control circuit i.e. lamp current control circuit 42 and a memory capacitor 48, while another terminal b thereof to a quenching control circuit 43. The output terminal of the lamp current control circuit 42 is connected to the observation lamp 20.

Figure 3:
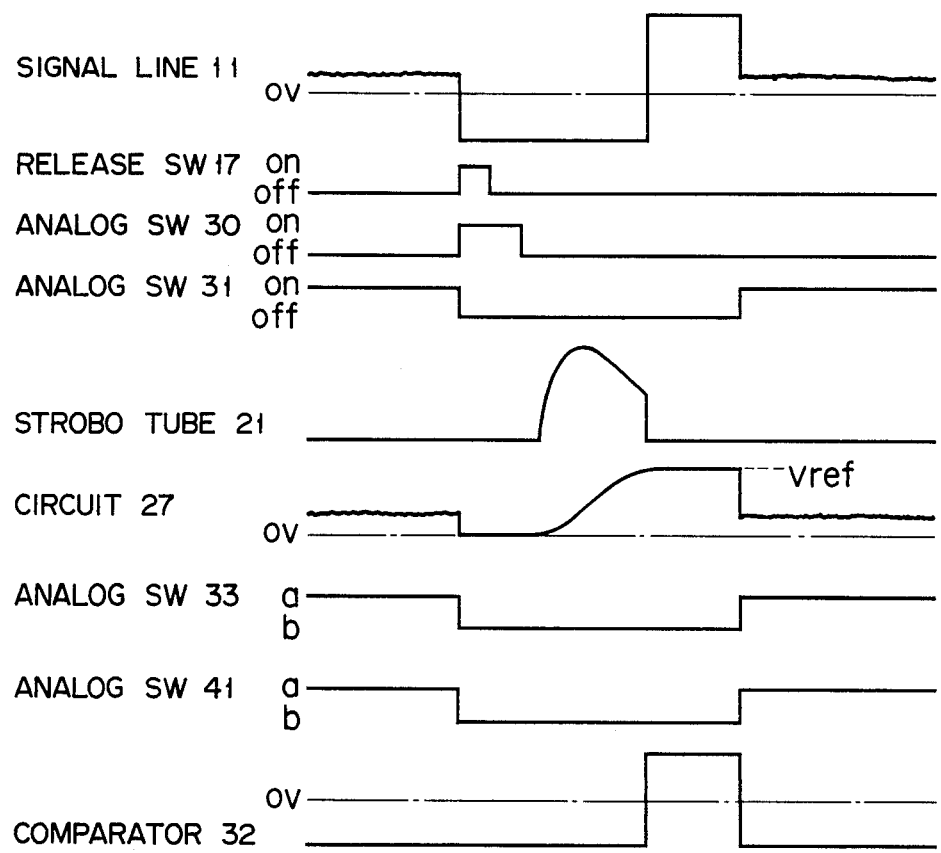
FIG. 3 is a time chart used to explain the operation of the circuit shown in FIG. 2.

The operation of the endoscope apparatus having such arrangement as described above will be described referring to the time chart shown in FIG. 3.

When the endoscope camera 5 is not used, namely, the release switch 17 is opened, the analog switch 30 is opened, the analog switch 31 closed and the analog switch 33 connected to the terminal a in response to timing signal of the timing circuit 35. The circuit 27 functions as current-voltage converter circuit under this state to convert photo-current signal of the photoelectronic element 15 to a voltage signal. This voltage signal is applied via the terminal a of the switch 33 to the buffer circuit 34. On the other hand, the switch driving circuit 44 causes the analog switch 41 to be connected to the terminal a in the light source unit 3. The photo-voltage signal is therefore supplied from the buffer circuit 34 to the lamp current control circuit 42 via the terminal 19b, signal line 11, terminal 25 and terminal a of the analog switch 41 as an observation light control analog signal. The voltage of the photo-voltage signal corresponding to incident light is compared with a reference voltage $V_{LT}$ through the lamp current control circuit 42 to control current flowing to the observation lamp 20 in such a way that voltage of photo-voltage signal becomes equal to the reference voltage $V_{LT}$, whereby the image of tissues in the body cavity can always be observed under certain brightness when observed through the eyepiece section of camera 5 if the foremost end of endoscope 1 is moved toward and backward tissues in the body cavity. In other words, so-called automatic light-controlled observation can be achieved. The capacitor 48 is intended to prevent the output of the lamp current control circuit 42 from fluctuating to flicker the observation lamp when the analog switch is switched over from the terminal a to the terminal b.

When the release switch 17 is closed to photograph, the analog switch 30 is closed, the analog switch 31 opened and the analog switch 33 connected to the terminal b. The integrating capacitor 28 is discharged and the circuit is reset to function as integrating circuit under this state. The switch driving circuit 44 in the endoscope camera 3 causes the analog switch 41 to be switched over to the terminal b in response to the release switch 17 closed. The shutter 14 is opened and the light path changeover mirror 23 operates to change over the light path. The timing circuit 35 causes the analog switch 30 to be opened at the time when the discharge of the integrating capacitor 28 is finished, thus enabling the integrating circuit 27 to start its integrating operation. The trigger circuits 39 and 40 supply trigger signals to the electronic flash tube 21 and main thyristor 38 at this time causing the electronic flash tube 21 to emit light. This light emitted comes incident upon the light guide 6 in the endoscope 1 after passing through the light path which has been changed over by the mirror 23 associated with the operation of the release switch 17. This incident light illuminates an object and light reflected from the object comes incident upon the beam splitter 16 in the camera 5 through the objective lens 8, image guide 7 and endoscope ocular lens 9. A part of light incident upon the beam splitter 16 or light reflected from the object is converted to photo-current by the photoelectric element 15. Output of the photoelectric element 15 is integrated by the integrating circuit 27 and then inputted to the comparator 32. This integrated signal is compared in voltage with the reference voltage Vref through the comparator 32 and when the voltage of the integrated signal reaches the reference voltage Vref, the output of the comparator 32 is inverted and then inputted to the quenching control circuit 43 via the terminal b of the analog switch 33, buffer circuit 34, terminal 19b, terminal 25 and terminal b of the analog switch 41 as a photographing light control distal signal. The quenching control circuit 43 supplies a trigger signal to the quenching thyristor 45 in response to the inverted output signal of the comparator 32 and renders the quenching thyristor 45 conductive, whereby the main thyristor 38 is reversely biased or made nonconductive by the discharge voltage of the quenching capacitor 46 to stop the light emission of electronic flash tube 21, that is, to enable automatic exposure photographing to be achieved. The timing and switch driving circuits 35 and 44 cause analog switches 30, 31, 33 and 41 to be returned to their original positions after the lapse of a predetermined time period, and the light path changeover mirror 23 and shutter 14 are also returned to their original positions. It takes only several tens or hundreds milliseconds that all of members return to their original positions after the shutter switch 17 is operated.

The above-described embodiment enables tissues in the body cavity to be observed under certain brightness at the time of observation and photographed under optimum exposure without being influenced by noises at the time of photographing.

Another embodiment of the present invention will be described referring to FIGS. 4 and 5. The same parts as those in the embodiment and its variation described above will be represented by the same reference numerals and description on these parts will be omitted.

The terminal b of the analog switch 41 is connected through an amplifier 49 to an integrator circuit 50, whose output terminal is connected to a comparator 51. Plural integrating capacitors 52 are arranged in the integrator circuit 50 and switched over by a change switch 53. An analog switch 54 is connected to the switch 53 so as to short-circuit the integrating capacitors 52 through the switch 53.

Figure 4:
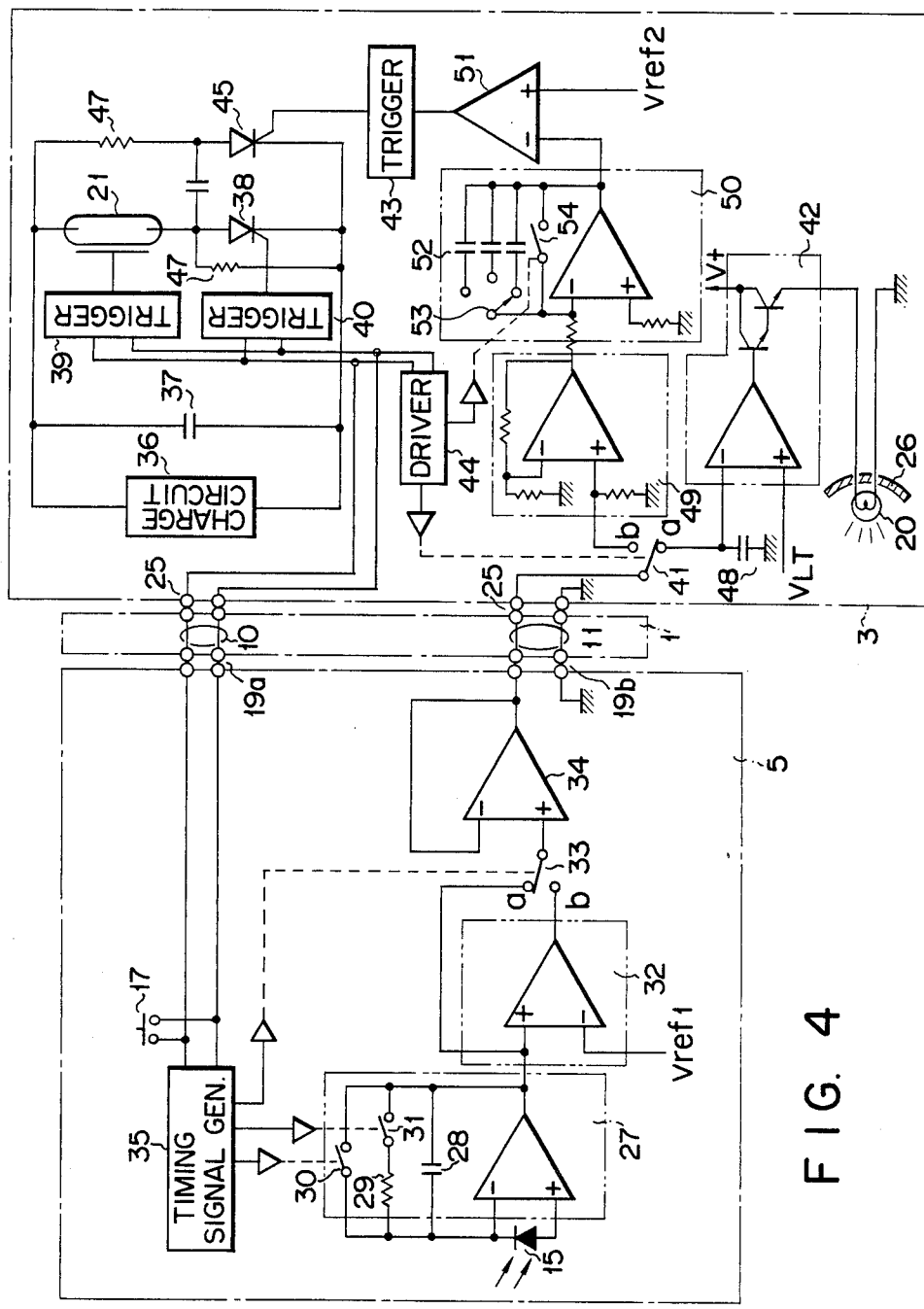
FIG. 4 is a circuit diagram of an endoscope apparatus according to another embodiment of the present invention.
Figure 5:
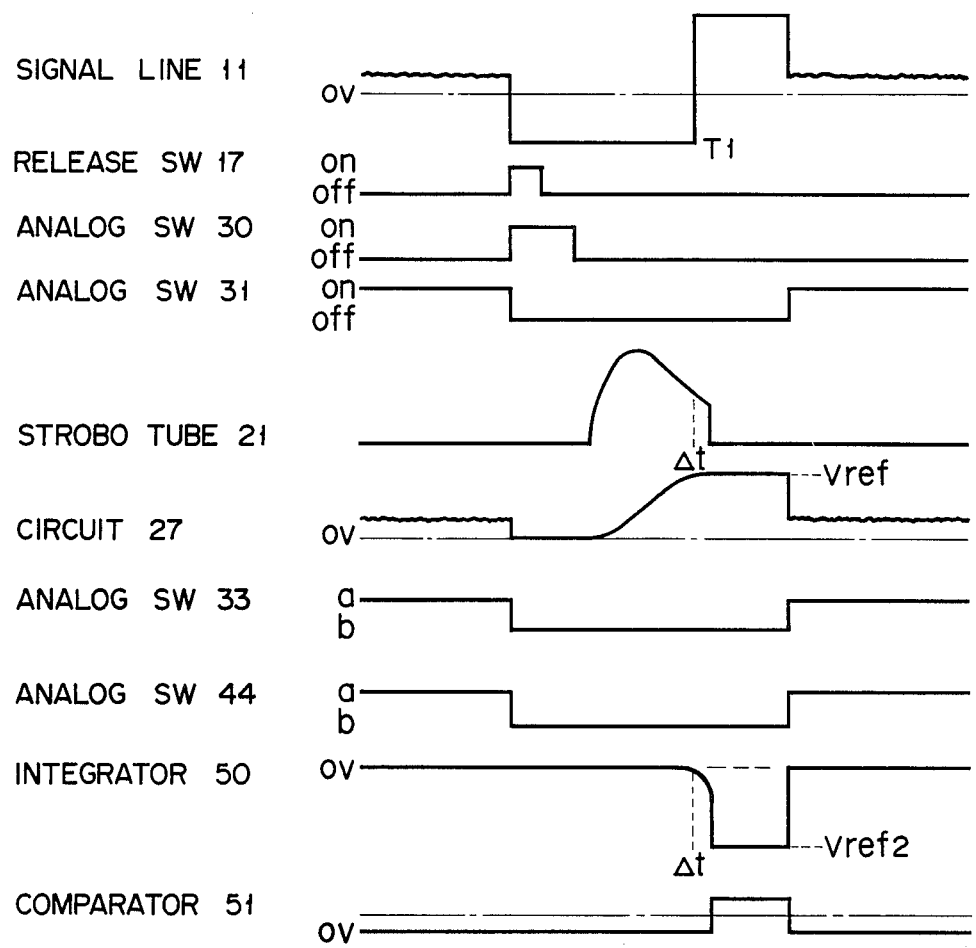
FIG. 5 is a time chart used to explain the operation of circuit shown in FIG. 4.
Figure 6:
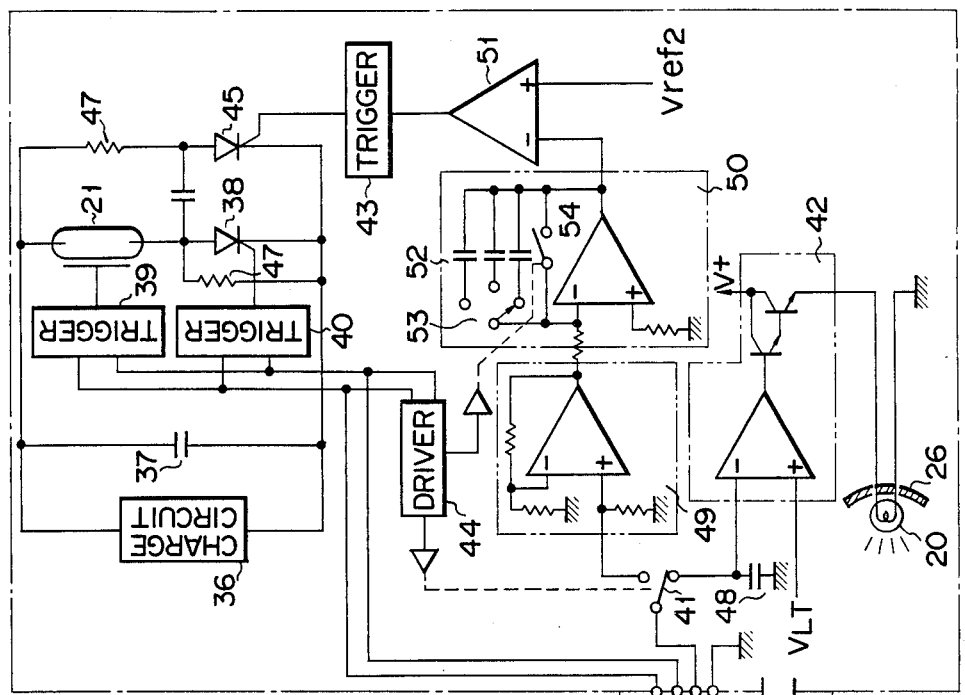
FIG. 6 shows a light receiving circuit arranged in the endoscope.
Figure 6:
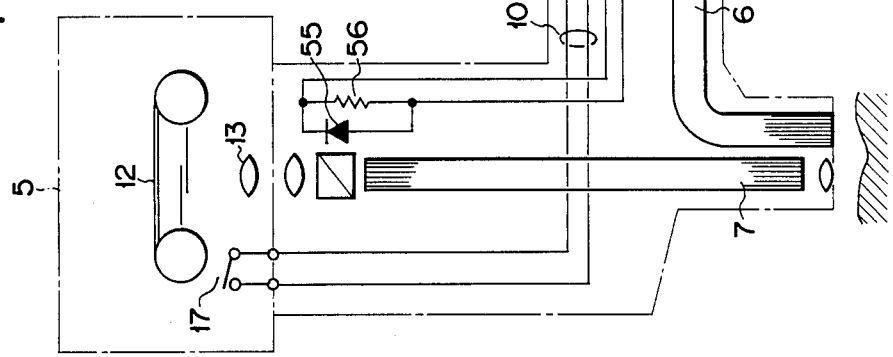

According to the endoscope apparatus shown in FIG. 4, photographing light control signal applied to the light source unit 3 from the camera 5 at the time of photographing, that is, the signal applied from the comparator 32 through the buffer circuit 34 is inputted to the amplifier 49 and amplified therethrough. This signal amplified through the amplifier 49 is inputted to the integrator circuit 50 and integrated therethrough. The integrator circuit 50 is adapted to integrate the output signal of the amplifier 49 correspondingly to the integrating capacitor 52 selected by the change switch i.e. sensitivity setting switch 53. This signal integrated through the integrator circuit 50 is inputted to the comparator 51 and compared therein with reference voltage Vref2. Since the input signal applied to the integrator circuit 50 is high in voltage, the voltage of the integrated signal reaches the reference voltage Vref2 for a short time period $\Delta t$ and the output signal of the comparator 51 renders the quenching thyristor 45 conductive through the quenching control circuit 43. The integrating time period Δt can be changed depending upon the integrating capacitor 52 selected by the sensitivity setting switch 53. When the integrating capacitor 52 of small capacity is selected, the integrating time period Δt can be made so short as to be practically negligible. In contrast, when the integrating capacitor 52 of large capacity is selected, the integrating time period Δt can be made long. When the automatic exposure calculator circuit constructed by the amplifier 49, integrator circuit 50 and comparator 51 is arranged in the light source unit 3 as described above, automatically-exposed photographing can be achieved even if an endoscope in which a photoelectric element 55 and a load resistor 56 are housed as shown in FIG. 6 is used. In this case, one of the integrating capacitors 52 in the integrator circuit 52 is selected responsive to photo-voltage level obtained through the photoelectric element 55 and load resistor 56 in the endoscope, and automatically-exposed photographing can be achieved according to the type of the endoscope.

As described above, the present invention allows observation light control signal and automatic exposure signal to be applied to the light source unit at the times of observation and photographing, respectively, so as to achieve automatic observation light control and automatic exposure photographing under right condition. Therefore, the present invention enables the observation through the endoscope apparatus and the observation referring to the photos photographed by the endoscope apparatus to be precisely effected.

In the embodiment of FIG. 4 the camera generates a signal when a photograph is taken, said signal being supplied through the comparator 32 to the control signal line 11. The signal may be supplied through the line 11 with the movable contact of the analog switch 33 connected to the terminal a and with the analog switch 31 kept closed not to make the circuit 27 function as an integrating circuit. If this is the case, there will appear in the control signal line 11 a signal having the waveform of the flash irradiation of the electronic flash tube. This signal is processed by the integrator 50 and the comparator 51, thus accomplishing an automatic exposure calculation. Hence, the camera is operated under control of the light source unit 3.

Although the electronic flash tube is employed as photographing light source in embodiments of the present invention, the photographing light source is not limited to the electronic flash tube but a lamp may be used to function as both of observation and photographing light sources, enabling automatic exposure to be achieved by the shutter or the like arranged in the light source unit. A solenoid or the like for closing the shutter may be driven in this case instead of turning the quenching thyristor ON.

Further the lamp current control circuit 42 may control the phase of AC current which is supplied to the lamp 20, in order to control the observation light, instead of directly controlling the current supplied to the lamp 20. Still further, the observation light may be controlled by varying the aperture opening in case only one lamp is used for supplying both the observation light and the photographing light.

What we claim is:
1. An endoscope apparatus comprising:
an endoscope having a light guide for transmitting observation and photographing lights, an image guide for transmitting light reflected from an object, and an eyepiece section;
a camera detachably arranged at the eyepiece section of said endoscope and having light control signal producing means for producing selectively an observation light control analog signal corresponding to an intensity of light transmitted through the image guide and a photographing light control digital signal for terminating the emission of the photographing light, said light control signal producing means including a photoelectric element, an integrating circuit for integrating an analog signal of said photoelectric element and a comparator for comparing the integration signal of said integrating circuit with a reference signal to produce the photographing light control digital signal; and
a light supply unit including light source means for emitting the observation light and photographing light, observation light control means for automatically controlling an intensity of the observation light of said light source means correspondingly to the observation light control signal applied from said light control signal producing means in said camera, and photographing light control means for controlling a brightness of the photographing light of said light source means correspondingly to the photographing light control signal.

2. An endoscope apparatus according to claim 1, wherein said light control signal producing means in said camera includes photoelectric means for generating a photoelectric signal corresponding to an intensity of light transmitted through the image guide in said endoscope, and converter means connected to said photoelectric means and adapted to convert said photoelectric signal to observation and photographing light control signals selectively.

3. An endoscope apparatus according to claim 2, wherein said converter means includes circuit means for converting the photoelectric signal to a voltage signal under observation mode and integrating the photoelectric signal under photographing mode, and means for comparing an integrated signal of said circuit means and a reference signal to produce the photographing digital signal.

4. An endoscope apparatus according to claim 1, 2 or 3, wherein said observation light control means includes means for controlling the brightness of said observation light correspondingly to the level difference between the observation light control signal and reference signal.

5. An endoscope apparatus according to claim 1, 2 or 3, wherein said photographing light control means includes means for causing said light source means to emit the photographing light associating with the releasing operation of said camera and interrupting the light emission of said photographing light in response to the photographing light control signal.

6. An endoscope apparatus according to claim 4, wherein said light source means has a halogen lamp for the observation light and said observation light control means is adapted to control current supplied to said halogen lamp.

7. An endoscope apparatus according to claim 5, wherein said light source means has an electronic flash tube for the photographing light and said photographing light control means is adapted to control the light emitting time period of said electronic flash tube.

* * * * *